United States Patent [19]

Harvey

[11] Patent Number: 5,057,019

[45] Date of Patent: Oct. 15, 1991

[54] COMPUTERIZED FACIAL IDENTIFICATION SYSTEM

[75] Inventor: David W. Harvey, Youngsville, N.C.

[73] Assignee: Sirchie Finger Print Laboratories, Raleigh, N.C.

[21] Appl. No.: 289,254

[22] Filed: Dec. 23, 1988

[51] Int. Cl.⁵ .............................................. G09B 19/00
[52] U.S. Cl. ................................................... 434/155
[58] Field of Search ......................................... 434/155

[56] References Cited

U.S. PATENT DOCUMENTS

| 2,974,426 | 3/1961 | McDonald | 434/155 |
| 3,896,565 | 7/1975 | Quinn, III | 434/155 |
| 4,045,883 | 9/1977 | Ryan | 434/155 |

FOREIGN PATENT DOCUMENTS

| 1388942 | 3/1975 | United Kingdom . |
| 1546072 | 5/1979 | United Kingdom . |
| 1605135 | 1/1982 | United Kingdom . |

Primary Examiner—William H. Grieb
Attorney, Agent, or Firm—Edward M. Farrell

[57] ABSTRACT

A process for creating a facial identification data base using a digital data processing computer system is provided. Entire photographic images of persons are first displayed and picked up by charge coupled solid state image sensors in a camera to produce electrical signals corresponding to the facial images. The sensors are horizontally and vertically disposed within the camera. The electrical signals are serially applied from the sensors to the computer system, where they are digitized and displayed onto the graphics monitor screen. Specific parameters relating to portions of the partial images to be stored are then inserted into the computer. The parameter data is then used to produce partial digitized images representing specific areas of said entire facial images, such as the forehead, nose, mouth or chin. The partial digitized images are produced by masking other areas of the total digitized image. The partial digitized images are then applied to a storage device such as a hard disk to provide the data base. The stored partial digitized images may then be selectively applied to a visual display means such as a television screen. Different partial images are selectively combined with other partial images to cause different total facial images to be selectively displayed.

9 Claims, 6 Drawing Sheets

COMPUTERIZED FACIAL IDENTIFICATION SYSTEM

BACKGROUND OF THE INVENTION

Facial identification systems are well known. Such systems have included using images from drawings or photographs of portions of faces, such as forehead, eyes, nose, mouth and chins. These images are used to build facial composites by selecting and changing the image portions until a desired facial composite is developed according to a description of a witness or victim of a suspect in a crime, for example.

Some patents illustrating facial identification systems involving manually selecting images of portions of faces to produce composite facial images are disclosed in Pat. Nos. 2,974,426 and 4,045,883.

Computerized facial identification systems which allow an operator to develop facial composites of an unknown suspect are also known. In these systems a data base of images is provided which include forehead, eyes, nose, mouth and chin sections. Some patents which disclose such computerized systems include British Pat. Nos. 1,388,942, 1,546,072 and 1,605,135. Such images may be derived from actual photographs.

The present invention is directed primarily to the preparation of a data base which stores digitized portions of a total digitized image in a storage medium, such as a hard disk. The partial digitized images are derived from full facial photographs of real persons taken by a camera and not by scanning photographs of partial images such as a forehead, nose or the like to provide data for digitizing.

Previous systems including the one discussed in the British Pat. No. 1,605,135 appear to involve creating an information storage system containing a plurality of digital records which are derived by a scan of elementary areas of each of a plurality of photographs of a face or parts thereof. Selected records are adjusted or modified in a computer and combined with other records to provide a visual display.

The system disclosed in British Pat. No. 1,605,135, for example, has a number of disadvantages in the creation of the data base. For example, it is difficult to create the photographs used to provide the data base material without initially including other undesired data, such as, background and other characteristics of the photographs which require elimination or modification before the desired data can be stored. Data attained by directly scanning a photograph is not readily modified and generally requires additional complex steps and equipment to achieve the data base with only the portions of the image.

OBJECTS OF THE INVENTION

It is an object of this invention to provide an improved method of creating a data base for a facial identification system from facial photographs of real people.

It is a further object of this invention to provide an improved computerized facial identification data base from electrical signals derived directly from sensors in a camera developed from photographs of real people.

It is still a further object of this invention to provide an improved computerized facial identification data base which includes partial digitized facial images of portions of a photographed face which may be selectively changed on a television screen to display different full facial images in accordance with an oral description.

BRIEF SUMMARY OF THE INVENTION

In accordance with the present invention, a process for creating a facial identification data base using a digital data processing computer system is provided to produce partial photographic digitized images of real people. An entire photographic facial image of a person is first displayed. A camera having sensors picks up the photographic image to produce corresponding electrical signals. The electrical signals from the sensors are then digitized in the computer. Specific image parameters of partial images to be stored in the data base are then initialized to produce partial digitized images representing portions of the entire facial image such as the forehead, nose, mouth and chin. The partial digitized images are achieved by masking or blocking out areas of the entire image which is not to be stored. The partial digitized images are then applied to a storage device to provide the data base which can be used to produce different composite facial images by selecting different partial digitized images to be visually displayed.

Other objects and advantages of the present invention will be apparent and suggest themselves to those skilled in the art, from a reading of the following specifications and claims:

DESCRIPTION OF THE INVENTION

The present invention is directed primarily to the creation of a data base by a computer, which will include a plurality of digitized portions of a face taken from a photograph. A camera produces electrical signals corresponding to the photograph. The position of the photograph and the controls in the camera are utilized so that only the picture in the photograph and it's surrounding white background are picked up by the camera. The white background surrounding the image causes the camera to produce electrical signals for this image area that is much higher in value to that of normal facial image signals. This arrangement is used so that no data which is not pertinent to the facial image is stored in the data base. The electrical signals produced in the camera are fed out of the camera to the computer and used to digitize the entire photograph facial image.

After the entire image is digitized in the computer process, portions of the digitized image are blocked out so that only the portions of the total image are stored in the data base. The portions stored may relate to eyes, nose, mouth, forehead and chin or other elements. The digitized partial images or portions selected to be stored are determined by specifying the parameters of the partial images and applying them to the computer. The partial digitized images are then applied to storage means, which may be a hard disk, and becomes a part of the data base.

Figure 1:
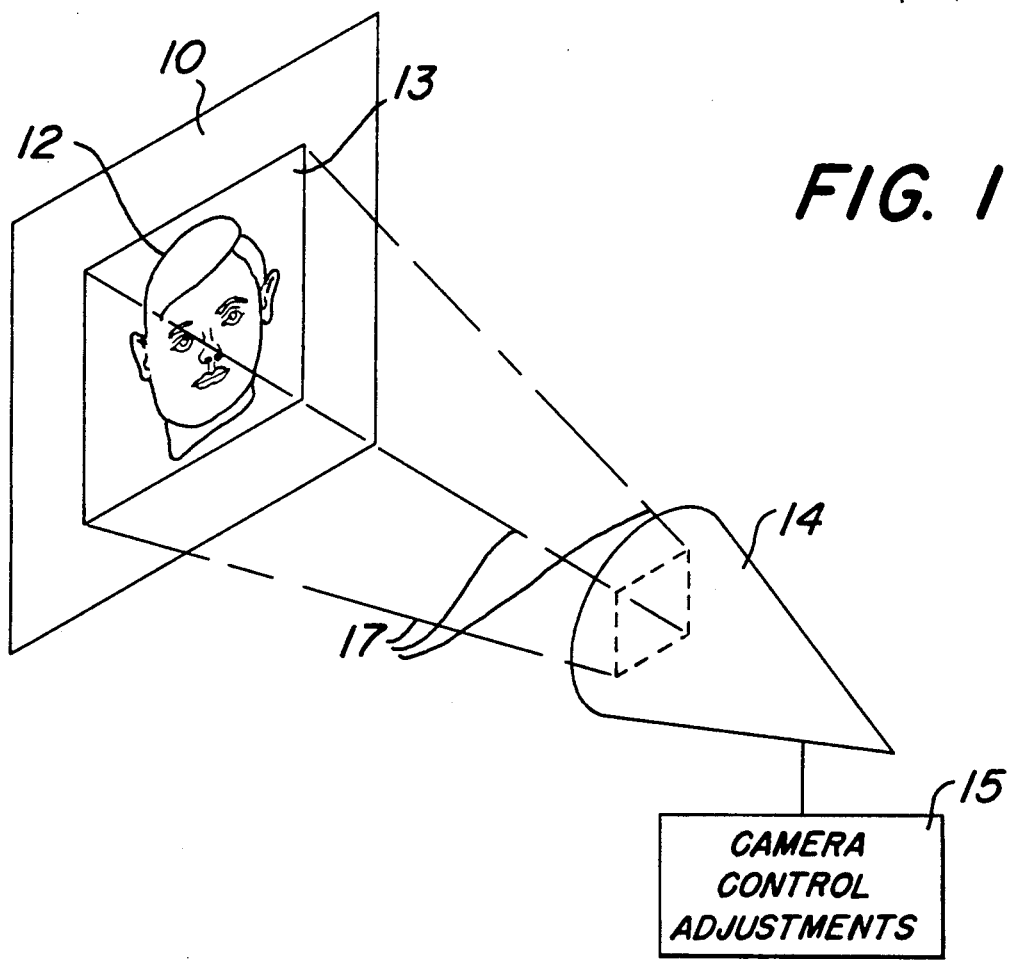
FIG. 1 is a sketch illustrating a facial photograph displayed to be picked up by a camera.

Referring to FIG. 1, a frame 10 includes a photograph of a facial image 12 mounted on a solid white background 13. A video camera 14 is disposed to pick up the facial image 12. The camera 14 is of a type which includes a plurality of sensors which are disposed horizontally and vertically within the camera to produce electrical signals corresponding to the elements in the photograph including the image 12 and white background 13. The camera 14 may be of a conventional type such as a video camera module XC-37/38/39 manufactured by Sony. The camera 14 may include control means 15 therein to provide focusing, zooms and the like. The frame 10 may be suitably positioned on a table or other support structure(not illustrated) within range of the camera 14. The camera 14 is adjusted by a zoom and/or other elements to correctly size, focus, etc., the facial image to the specific image parameters selected for the desired image to be used in the data base to be created. Lines 17 illustrate how the image and white background are picked up without picking up other areas in the environment of the photograph.

Figure 2:
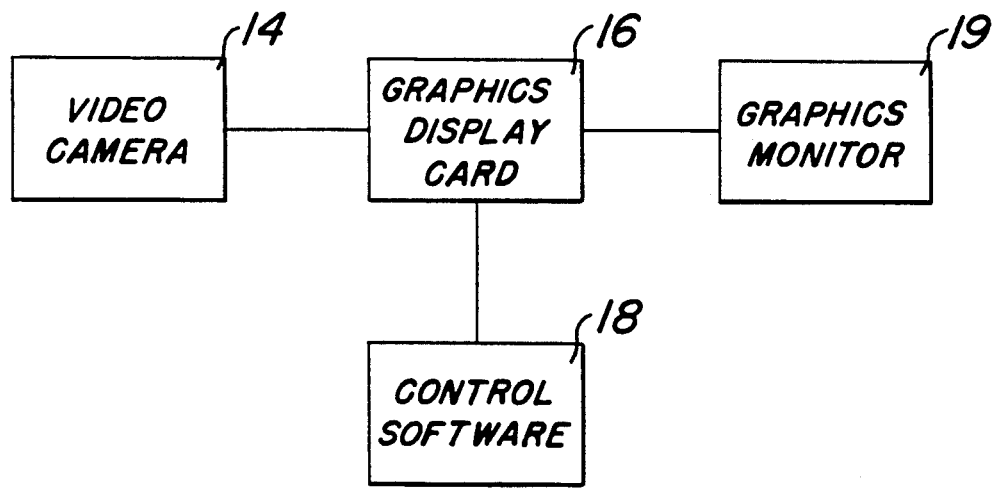
FIG. 2 is a block diagram illustrating some of the preliminary steps for utilizing electrical signals from the camera and producing a visual display of the photograph.

Referring to FIG. 2, the video camera 14 (FIG. 1) generates electrical signals which are serially stepped out of the camera and applied to a graphics display card 16. Control software material or programs is applied from control means 18 to the graphics display card 16. The control means 18 modifies or changes the information at the graphics display card which is applied to a graphics monitor 19. Control means 18 includes the capability to modify the electrical signals being sent to the graphics monitor 19 by the graphics display card 16 by adjusting the relative brightness and/or contrast of the displayed image. A control element to adjust the threshold is also available that has no visual effect on the displayed image but sets a level at which an image data element is determined to be true image data or true background data during the digitizing process of the image portion.

Figure 3:
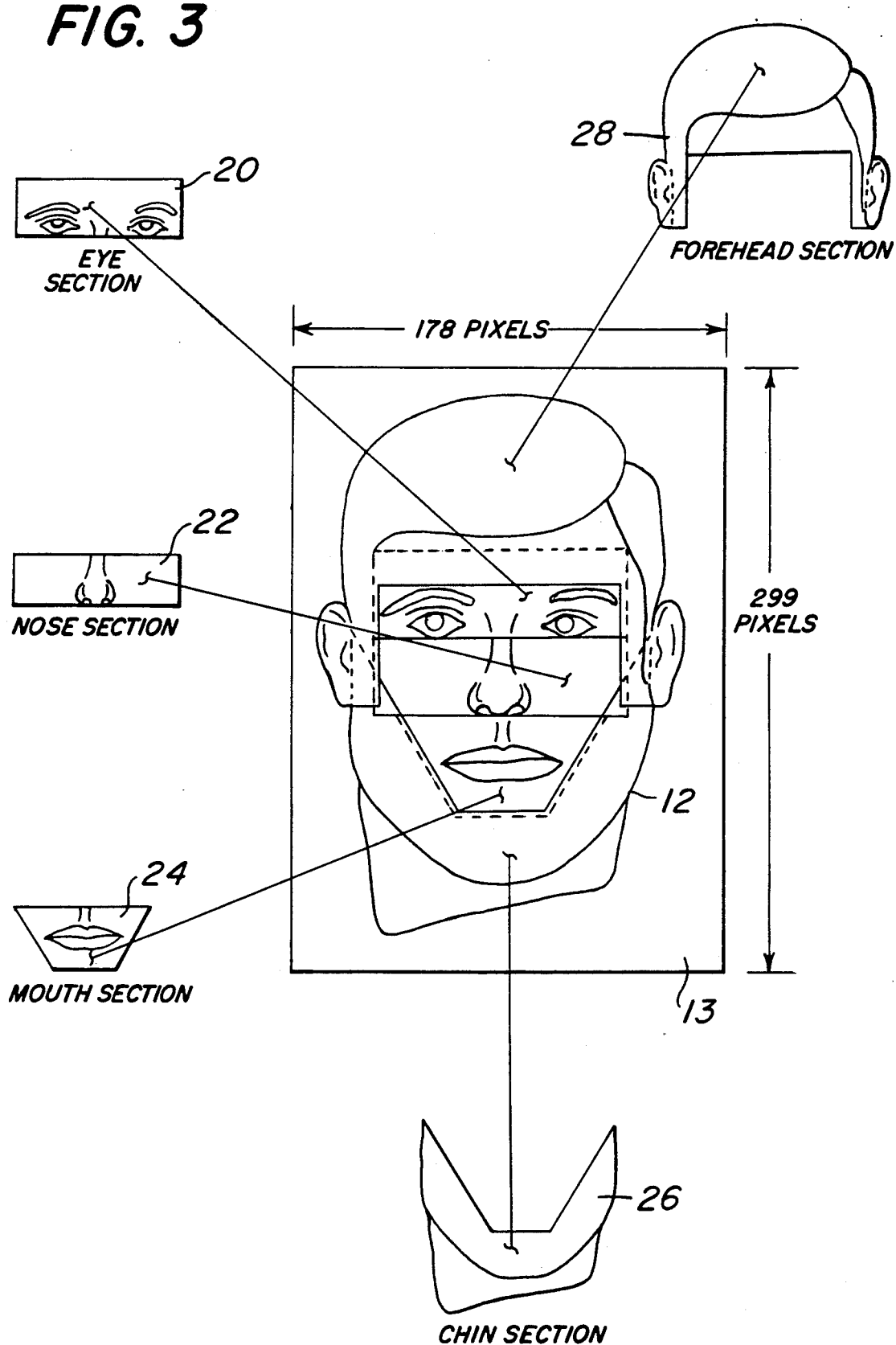
FIG. 3 illustrates a facial image including dividing lines illustrating how the image is broken down into different portions or partial images of the photograph.

Referring to FIG. 3 the image 12 and background 13, which corresponds to the image and background of FIG. 1, includes a number of lines which subdivide the total facial image 19 into sections, such as eye section 20, nose section 22, mouth section 24, chin section 26 and forehead section 28. The image 12 and white background 13 in the example illustrated includes 178 horizontally extending pixels or elements and 299 vertically extending pixels or elements. In one example, these pixel elements are mapped into a space of 512 pixels or elements horizontally and 480 pixels or elements vertically. These pixel elements may, for example, correspond to a similar number of sensors in the camera 14 (FIG. 1) which pick up the total facial image and white background.

Figure 4:
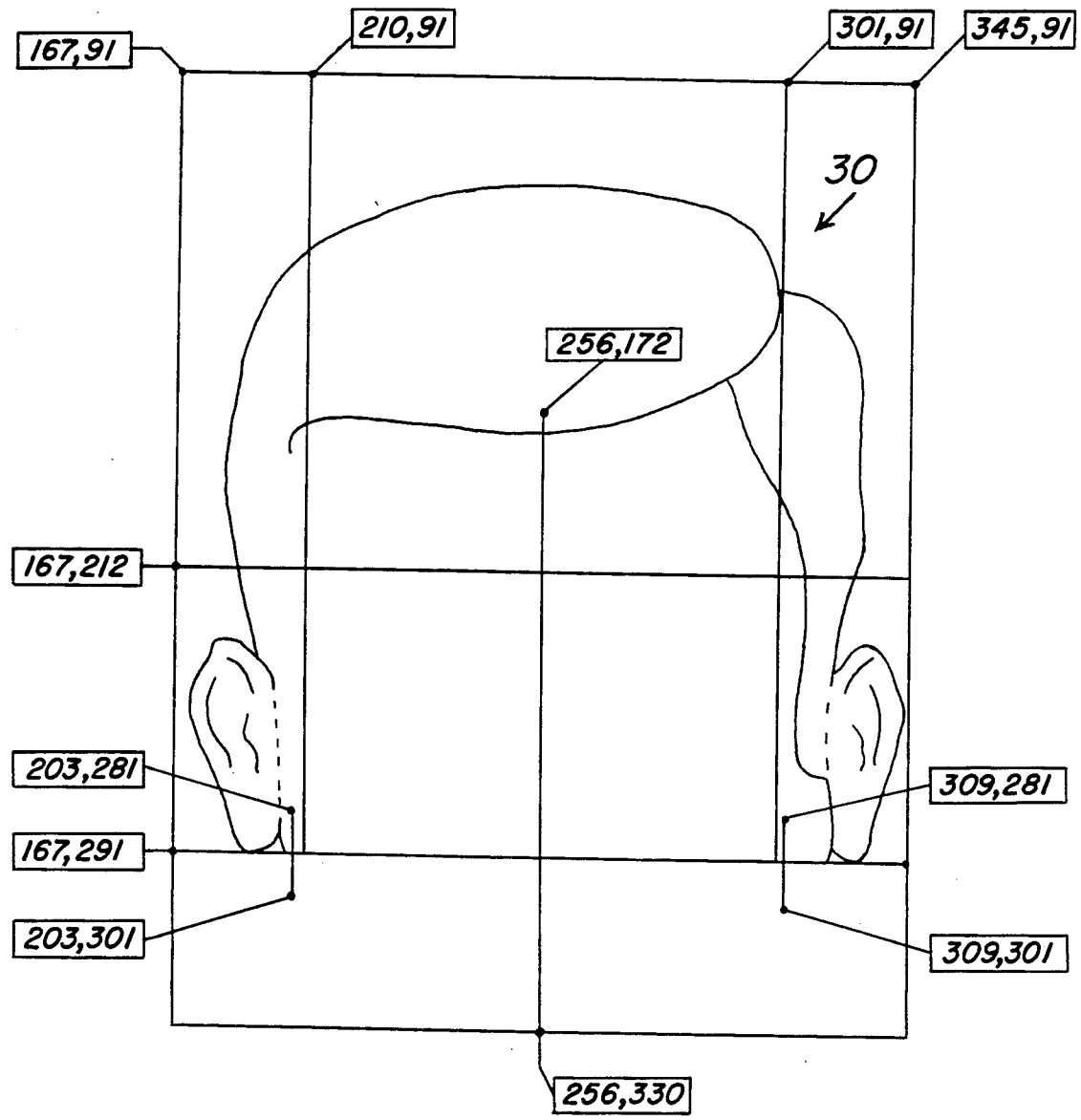
FIG. 4 illustrates a forehead image frame which will be used in describing the overall system.

Referring to FIG. 4, the portion 30 relates to the forehead section 28 in FIG. 3. In the example illustrated, the hair is also illustrated. Other sections 20, 22, 24 and 26 in the image 12 of FIG. 3 would be processed in the same or similar manner as the forehead section. Consequently only the image or portion illustrated in FIG. 4 to the forehead will be described in detail with respect to how the partial images for the data base are created by the computer.

Basically, the present invention relates to the concept of first digitizing the entire facial image such as the image 12 illustrated in FIG. 3, and then selectively using portions of the total digitized image to produce partial digitized images relating to particular parts such as the sections 20, 22, 24, 26 and 28 (FIG. 3). This is accomplished by blocking out or masking areas of the total image not to be stored in the data base and comparing the image data to the threshold to distinguish image data from background data to be stored in the data base. For example, when it is desired to store a digitized image such as the forehead 28, all the remaining portions in the photograph 19 are either masked, blocked, or compared to the threshold. After the forehead has been digitized and applied to the data base, the other elements of the facial image 19 may be digitized to provide partial images which are stored in the data base also.

The various 2-number sets, such as "167,91" illustrated in FIG. 4 indicate the relative position in the digitized image by an "x,y" coordinate system of an image occupying a space of 512 pixels or elements horizontally and 480 pixels or elements vertically. The "x" pixel or element, in this case "167", represents the relative horizontal position from left to right from an originating point "0.0" located at the first pixel element in the digitized image as displayed on the graphics monitor that is located at the upper left corner of the image. Likewise the "y" component represents the 'yth' pixel or element in the image, or in this case "91", running vertically down from the origin "0.0" at the top left corner of the digitized image as displayed on the graphics monitor to the 91st pixel or element of the image. Other sets of numbers illustrated represent particularly X, Y positions.

Figure 5A:
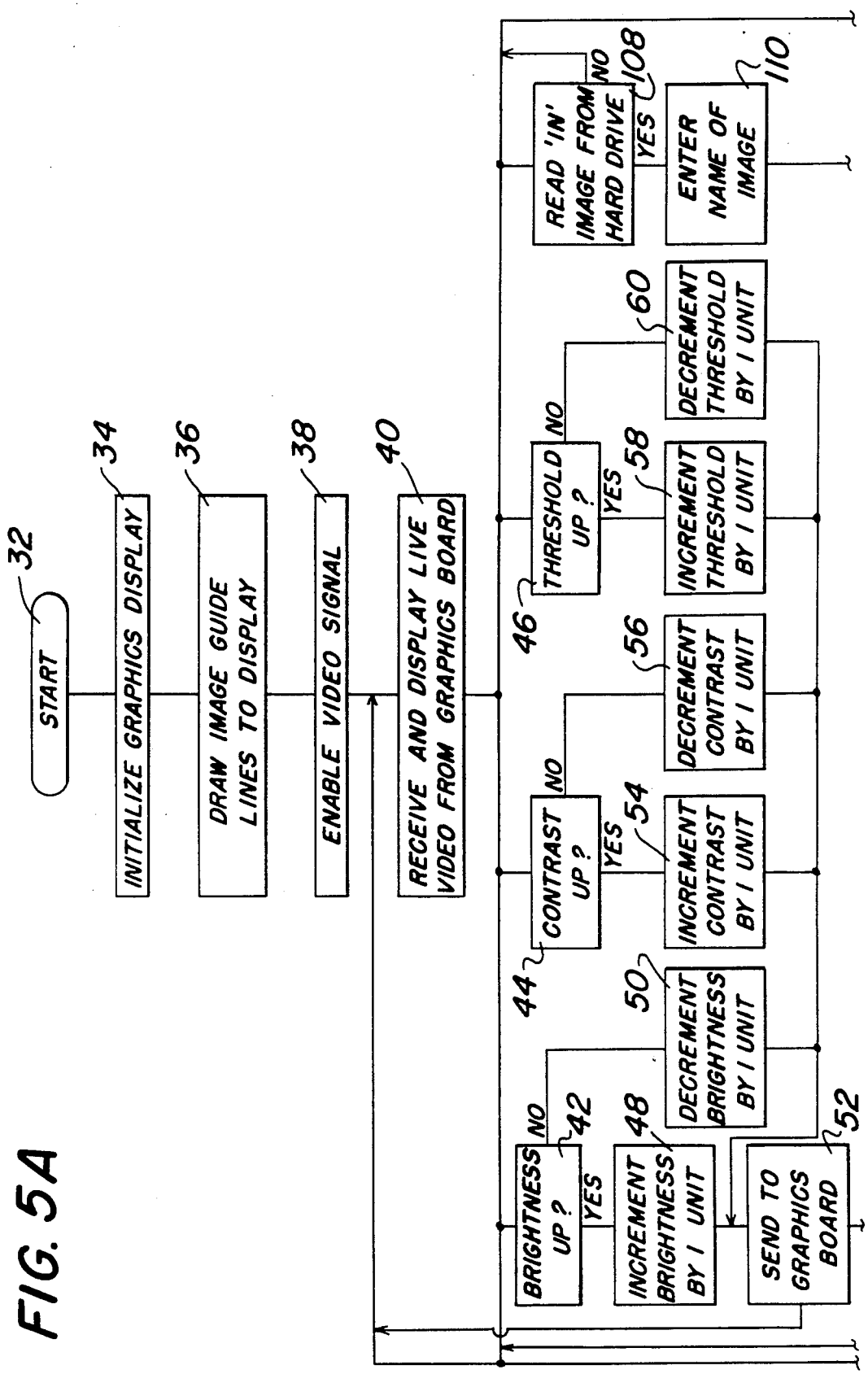
FIG. 5 is a block diagram of an image digitizing flow chart, in accordance with the present invention.
Figure 5B:
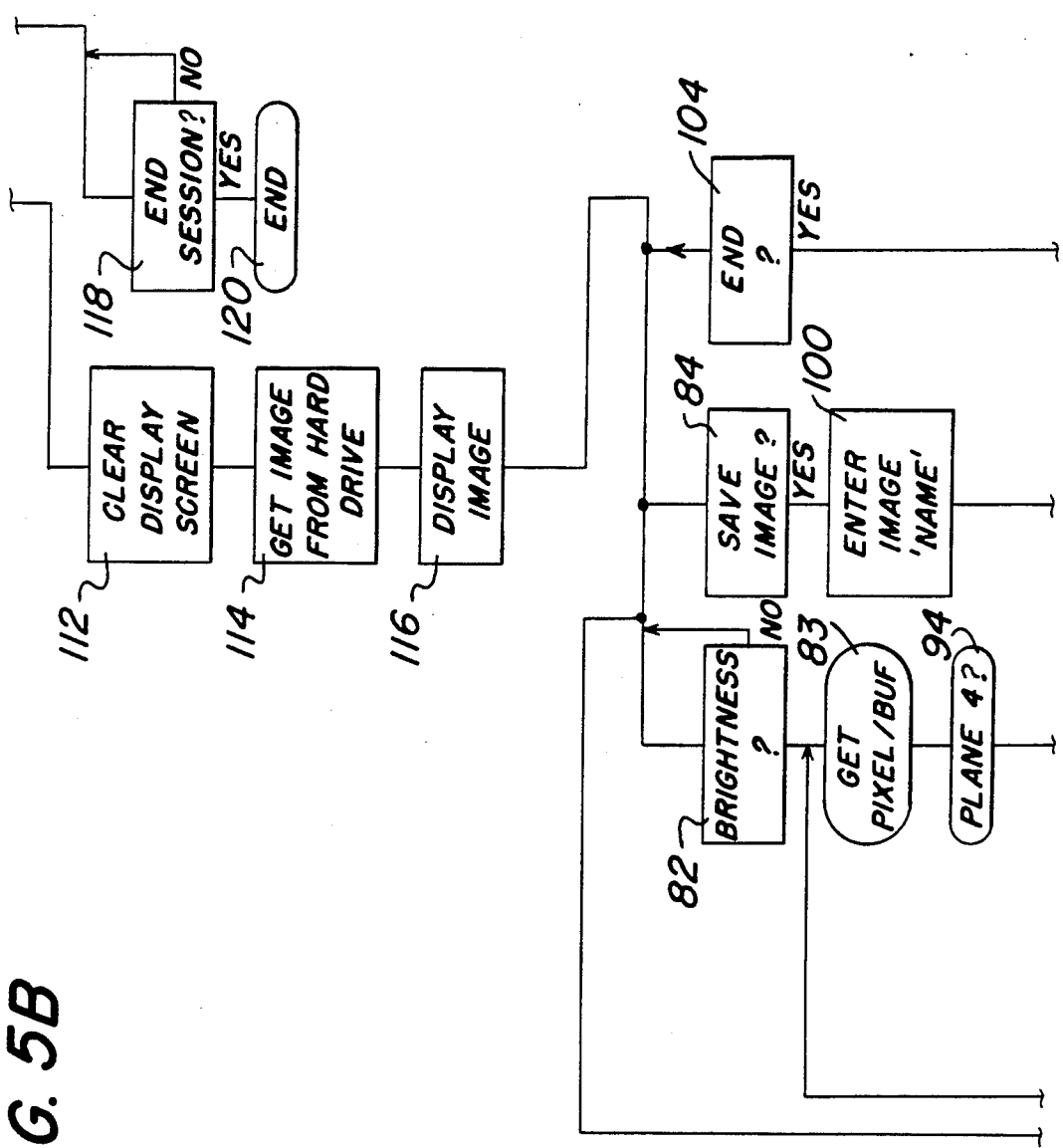
Figure 5C:
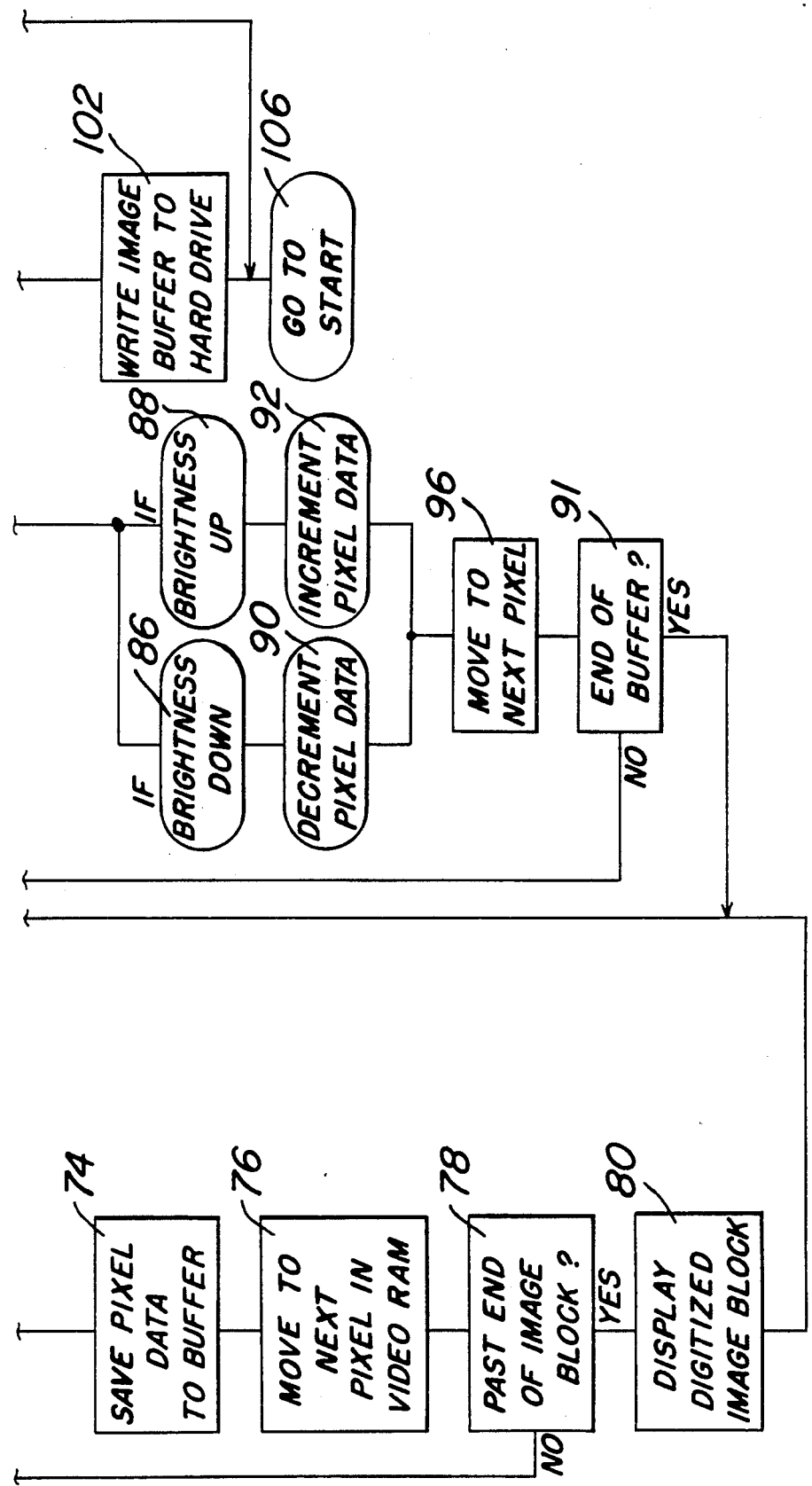

Referring to FIG. 5, the image digitizing flow chart includes a start step at position 32, at which time a graphics display or a facial photograph becomes effective at the display means 34. The lines relating to the photograph illustrated in FIGS. 1 and 3 are then drawn so that proper positioning and sizing of the image may be accomplished by way of camera control means 15 (FIG. 1). A television picture is enabled at step 38. At this time the image 12 as illustrated in FIG. 1, is displayed for example in a television picture. The video picture at point 40 displays a live video image from the graphics display card 16 (FIG. 2). The television picture is then viewed and various adjustments to the picture may be made.

Brightness control 42, contrast control 44 are adjusted if needed, modifying the television picture at point 40. Threshold level control 46 may also be adjusted but does not affect the television picture at this point, but rather, the digitized data at point 72. The brightness control may increase the brightness by a control element at point 48 or decrease the brightness by a control element at point 50. The change in the brightness is sent back to the point 40 through a buffer at point 52.

In like manner, a change in contrast at point 44 is either increased or decreased by elements at points 54 and 56 respectively, and sent back to the point 40 through block 52. Finally, the threshold control at point 46 is changed up or down by elements at points 58 and 60 and returned to point 40 through point 52.

When the picture at the point 40 is at the desired display, it is transmitted and digitized at digitizing point 62. The digitized image, which at this point includes the entire image 12 (FIG. 3) is applied to a video memory 64. The entire digitized image is applied to a mask means at 66 which makes use of so called level "4" signals during the masking process.

In a masking operation, the system involving the present invention utilizes a masking process which distinguishes true partial image data to be stored in the data base from extraneous data not involving the partial image. Such extraneous data may involve the white background 13 of FIG. 1, various dividing lines extending into sections of other partial images not to be reproduced and other materials.

Brightness and other factors determine whether or not certain data is part of the partial image to be reproduced for the data base. For example, brightness may be considered as varying from black to white and at levels therebetween. These levels may be considered as varying from 0-255, for example, with "0" representing black and "255" representing white. In the example of the invention being described, a Level "4" was assigned to all unwanted data, such as background and all other material except the partial image data. Level "4" signals for example, were used to produce a blue background on a television screen. Level "4" signals were also used to mask all other portions of total digitized facial image to produce only the partial image desired to be stored in the data base.

The Level "4" signals used for masking may be considered as code signals. When they are inserted into the image data, the Level "4" signals determine whether or not to place the image portions.

A step of initializing the specific image parameters at point 68 takes place and is used with the masking step. For example, if the forehead is the portion of the image to be stored in the data base, the particular pixel elements relating to the forehead are specifically defined at this point. All of the other pixel elements in the entire image except the forehead, for example, is masked or block out so that only the intended forehead image portion passes through the remaining steps of the system.

The particular positions of the pixel elements are illustrated in FIG. 4, where the double numbers illustrate the horizontal and vertical positions of the pixels. As previously discussed, the numeral "167,91" illustrates a pixel at a horizontal point 167 in the total image and a vertical point 91 in the image displayed in FIG. 3. The pixel data is obtained at point 70 and applied to threshold control 72 where various elements representing the image are compared with a pre-determined threshold level, which may for example relate to background depending upon the level of the image pixel at various points.

Parts of the image may be changed to a plane "4" level at point 73. A signal from the threshold 72 is applied to a buffer 74. The system then moves the next pixel into the video random access memory 76 currently holding the digitized unprocessed image. The data is then passed through point 78 which determines whether the end of the partial digitized image has been reached and, if not, control is returned to point 70 to continue the processing. When the end of the desired image has been reached, the contents of buffer 74, which now represents a partial digitized image, are then displayed at point 80 and applied to to brightness block 82, save image block 84 and end image block 104.

If a change in brightness is desired to the particular partial image prior to storage, the brightness is changed at points 86 and 88. The signal from brightness block 82 passes through pixel buffer 83 and block 94. Control block 94 compares the current image pixel for a plane "4" level. This block 94 is not intended to change the level "4" but rather just the image data of the partial digitized image. If a level "4" level is found, then control is transferred to block 96 to move the image pixel pointer to the next pixel of the image after which block 90 checks to see if the end of the partial digitized image has been reached. If it has, control is transferred back to brightness control block 82, save image block 84 and end block 104. If a level 4 level is not found at block 94 then the pixel must represent true image data and the appropriate function is initiated by either brightness down block 86 or by brightness up block 88.

If the partial image from point 80 is to be saved at point 84, the name of the partial image is inserted at the point 100. A write buffer 102 is actuated to apply the partial image to a hard disk drive, or other type of storage. The end is indicated at point 104 and a return to start is indicated at 106.

A section is provided to read in an image from a hard disk drive at point 108. The name of the desired image is entered at point 110. A step of clearing the display screen is initiated at point 112. The image is obtained from the hard drive at point 114 and an image is displayed at point 116 and applied to brightness block 82, save image block 84 and end block 104.

The "end" or "no end" of a session is indicated at point 118 and the "end" is indicated at point 120.

The various steps in the process illustrated in FIG. 5 are capable of being performed by a conventional digital computer, for example a computer including conventional processors and monitors such as an IBM XT in combination with conventional video digitizing card and Microvitec RGB color monitor may be used.

After a plurality of digitized images of all the various elements relating to the portions of the faces are completed, they are properly identified and included in a memory device, which may be a hard disk. The data base may be included as part of a computerized facial identification system that allows an operator to quickly and easily develop a facial composite of an unknown suspect from a description given by a witness or victim of a crime.

The data base utilizes images which are comprised of forehead, eyes, nose, mouth and chin sections. All of these images are used to build the facial composite by selection from a keyboard. In addition to the images mentioned, accessory images may be provided in the data base as well. These images include mustache, beard, eye glasses and headwear.

All of the images in the data base are referenced from an image index that may be provided with a system. The index assists a witness or victim to select the image sections that he or she feels most closely resembles the suspect. The images may be cataloged by type and each may be assigned a numeral number that coincides with the image on the data base. The images pictured in the index are shown as they would appear on a graphic monitor when they are called up for display and/or composition.

Among the chief features of the present invention involves the use of a camera which may be controlled to pick up only the entire facial image with some predetermined amount of background which may be readily digitized without picking up extraneous matter which later has to be eliminated prior to using the data to create the data base. The partial images of the total image are created by blocking out portions of the entire digitized facial images to derive partial digitized images which are readily stored.

What is claimed is:

1. A process for creating a facial identification data base using a digital data processing system by digitizing and storing partial photographic images of the faces of real people comprising the steps of:
   a. displaying an entire photographic facial image of a person;
   b. providing a camera having sensors therein to receive said entire facial image to generate electrical signals corresponding to said facial image;
   c. visually displaying said entire facial image from said camera;
   d. adjusting said camera to pick up the entire facial image free of extraneous matter not required for creating said data base;
   e. digitizing and electrical signals corresponding to said entire facial image form the sensors of said camera;
   f. initializing specific image parameters of part of the digitized entire facial image from said camera to produce a preselected partial digitized image to block out other portions of said entire facial images, and
   g. storing said partial digitized image for use in producing composite facial images when combined with other partial stored digitized partial images.

2. A process as set forth in claim 1 wherein a coded signal for producing a pre-determined signal level is used in the step of blocking out said other portions of said facial image.

3. A process as set forth in claim 1 wherein a further step includes visually displaying said partial digitized image prior to storing to permit steps for adjusting said partial digitized image.

4. A process as set forth in claim 3 wherein one of the steps for adjusting said partial digitized image prior to storing includes comparing the signal level of said partial digitized image with a pre-determined and adjustable threshold signal level to indicate the presence and absence of the partial image.

5. A process as set forth in claim 4 wherein incoming signals including said partial digitized image are used in said step of comparing so that said incoming signals that are equal to or exceeding said threshold level, indicating non-image and background data, are converted to said pre-determined signal level by said coded signal, with the incoming signals that are below said threshold level signal indicating partial image data are subsequently stored.

6. A process as set forth in claim 5 wherein an additional step includes assigning a name to said partial digitized image prior to said step of storing.

7. A process as set forth in claim 6 wherein an additional step includes storing said partial digitized image on a hard disk in said facial identification data base.

8. The process as set forth in claim 7 wherein a plurality of partial digitized images are derived and stored from a plurality of entire facial images.

9. The process as set forth in claim 8 wherein said plurality of partial digitized images represent sections of said plurality of facial images including eyes, noses, mouths, foreheads and chins.

* * * * *

UNITED STATES PATENT AND TRADEMARK OFFICE
CERTIFICATE OF CORRECTION

PATENT NO.  : 5,057,019

DATED       : October 15, 1991

INVENTOR(S) : David W. Harvey

It is certified that error appears in the above-identified patent and that said Letters Patent is hereby corrected as shown below:

Column 7, line 1, cancel "and" and substitute therefor -- said--.

Column 7, line 2, cancel "form" and substitute therefor -- from--.

Signed and Sealed this

Twenty-sixth Day of January, 1993

Attest:

STEPHEN G. KUNIN

*Attesting Officer*    Acting Commissioner of Patents and Trademarks